(12) United States Patent
Bruheim et al.

(10) Patent No.: US 8,470,876 B2
(45) Date of Patent: Jun. 25, 2013

(54) LIPID COMPOSITION FOR THE TREATMENT OF SKIN PROBLEMS IN COMPANION ANIMALS

(75) Inventors: Inge Bruheim, Volda (NO); Mikko Griinari, Espoo (FI)

(73) Assignee: Olini Ltd, Helsinki (FI)

( * ) Notice: Subject to any disclaimer, the term of this patent is extended or adjusted under 35 U.S.C. 154(b) by 56 days.

(21) Appl. No.: 13/132,382

(22) PCT Filed: Dec. 11, 2009

(86) PCT No.: PCT/IB2009/007937
§ 371 (c)(1),
(2), (4) Date: Aug. 2, 2011

(87) PCT Pub. No.: WO2010/067206
PCT Pub. Date: Jun. 17, 2010

(65) Prior Publication Data
US 2011/0288165 A1 Nov. 24, 2011

(51) Int. Cl.
*A61K 31/355* (2006.01)
*A61K 31/20* (2006.01)

(52) U.S. Cl.
USPC .......................................... 514/458; 514/560

(58) Field of Classification Search
USPC ................................. 514/458, 560
See application file for complete search history.

(56) References Cited

U.S. PATENT DOCUMENTS

2008/0213357 A1 9/2008 Hebard et al.
2008/0260929 A1 10/2008 Ursin et al.

FOREIGN PATENT DOCUMENTS

WO 03/099216 12/2004
WO 2007/056823 5/2007

OTHER PUBLICATIONS

Schoenherr, et al., "Nutritional modification of inflammatory diseases," Clinical Techniques in Small Animal Practice, Saunders, Philadelphia, PA, US, vol. 12, No. 3, Aug. 1, 1997, pp. 212-222.
Saevik Bente K, et al., "A randomized controlled study to evaluate the steroid sparing effect of essential fatty acid supplementation in the treatment of canine atopic dermatitis," Veterinary Dermatology, Jun. 2004, vol. 15, No. 3, Jun. 2004, pp. 137-145.

*Primary Examiner* — Raymond Henley, III
(74) *Attorney, Agent, or Firm* — Casimir Jones, S.C.

(57) ABSTRACT

The present invention provides lipid compositions comprising linolenic acid (LA), alpha-linolenic acid (ALA), stearidonic acid (SDA) and gamma linolenic acid (GLA), said LA and ALA in a ratio of about less than 2:1 LA:ALA. The compositions find use in for improving, treating, or preventing a condition selected from the group consisting of: eczema, dry skin, flaky skin, pruritus, pyotraumatic dermatitis, furunculosis, dry paw pads, rough paw pads, chapped paw pads, paw pad durability, dry rhinarium, chapped rhinarium, split claws, brittle claws, rashes, hairless spots, hot spots, symmetrical lupoid onychodystrophy, skin ulceration, skin crusting, reddening of skin between toes, external ear infection, and nutritional dermatosis.

10 Claims, 3 Drawing Sheets

LIPID COMPOSITION FOR THE TREATMENT OF SKIN PROBLEMS IN COMPANION ANIMALS

CROSS-REFERENCE TO RELATED APPLICATIONS

The present application is a U.S. 371 national stage entry of pending International Patent Application No. PCT/IB2009/007937, international filing date Dec. 11, 2009 (published as WO 2010/067206 on Jun. 17, 2010), which claims priority to expired U.S. Provisional Patent Application No. 61/121,721, filing date Dec. 11, 2008, and which claims priority to expired U.S. Provisional Patent Application No. 61/221,815, filing date Jun. 30, 2009, the contents of which are incorporated herein by reference in their entireties.

FIELD OF THE INVENTION

This invention is in the field of lipids and nutrition.

BACKGROUND OF THE INVENTION

Companion animals such as dogs and cats are frequently reported having skin and hair coat problems: dry skin, desquamation, pruritus, excessive shedding and dull hair coat. Long term skin problems increase susceptibility to infections and the severe cases of skin problems may develop into lesions (e.g. pyotraumatic dermatitis) and boils (e.g. furunculosis) which are often difficult to treat. Dietary strategies for prevention and treatment of skin problems and to complement or replace long term medicinal treatment have been explored [1, 2, 3]. Dietary formulations based on plant oils such as sunflower oil, olive oil, linseed oil, black currant seed oil, evening primrose oil, borage oil and fish oil, have been used to alleviate skin problems [4, 5, 6, 7, 8, 9]. Fatty acids such as linoleic acid (LA), alpha-linolenic acid (ALA), gamma-linolenic acid (GLA), stearidonic acid (SDA), eicosapentaenoic acids (EPA) and docosahexaenoic acid (DHA) are components of these oils and have been identified as the most important fatty acids with biological activity regarding skin health. In popular media and commercial messages involving dietary fatty acid supplements the ratio of dietary n-6 and n-3 of 5:1 is considered to be optimal. Expert committees have concluded that the n-6:n-3 ratio is not helpful and may in fact distort the analysis of dietary fatty acid intake data [10]. Use of simpler ratio of LA to ALA has been recommended until more is known about the relative potencies of various n-3 fatty acid types [10]. Because the enzyme that produces GLA from LA, $\Delta$-6 desaturase, has low activity in the skin, dietary GLA is thought to be important for skin health [11]. Combinations of dietary GLA and EPA are thought to be more effective than GLA alone with respect to skin health [7]. Thus, number of fatty acids with bioactivity towards the skin have been identified, but no consensus with respect to optimal fatty acid ratios exists. In humans, hempseed oil has been shown to be effective in treating patients with atopic dermatitis at a dose of 30 mL/day in a recently published clinical trial [12]. The type of hempseed oil used in this study is characterized by having a ratio of LA:ALA of 3:1, a ratio of GLA:SDA of 3:1, a ratio of LA:GLA of 14:1 and a ratio of ALA:SDA of 11:1.

SUMMARY OF THE INVENTION

This invention discloses a novel lipid mixture comprising hempseed oil, linseed oil and rapeseed oil. In some embodiments, the oils have been mixed in proportions that give LA:ALA ratio of at least 2:1 and the GLA:SDA ratio of at least 2:1. In some embodiments, the oil compositions have a ratio of LA:GLA of up to 20:1 and a ratio of ALA:SDA of up to 20:1 Furthermore, the invention discloses novel biological properties of this lipid mixture in the area of improved skin conditions in companion animals. In some embodiments, the oils can also be mixed in proportions that give LA:ALA ratio less than 2:1 (e.g. 1.9:1 to 1.99:1). In some embodiments, the oil compositions have LA:ALA ratios from about 1.5:1 to about 2.39:1. In some embodiments, the lipid compositions contain GLA+SDA at the level at least 3% of total fatty acids.

In some embodiments, the present invention provides lipid compositions comprising linoleic acid (LA), alpha-linolenic acid (ALA), gamma linolenic acid (GLA) and stearidonic acid (SDA). In some embodiments, the ratio of said LA to said ALA in said compositions is at least 2:1 and the ratio of said GLA to said SDA is at least 2:1. In some embodiments, the ratio of said LA to said GLA in said compositions is at least 10:1 and the ratio of said ALA to said SDA is at least 10:1. In some embodiments, the ratio of said LA to said GLA in said compositions is at least 20:1 and the ratio of said ALA to said SDA is at least 20:1. In some embodiments, the LA, said ALA, said GLA and said SDA in said compositions is obtained from linseed oil, rapeseed oil and hempseed oil. In some embodiments, the compositions further comprise a mixture of tocopherols. In some embodiments, the compositions are essentially free of EPA and DHA. In some embodiments, the present invention provides a lipid mixture comprising LA and ALA in a ratio of at least 2:1 and GLA and SDA in a ratio of 2:1 effective on alleviating skin problems in companion animals.

In some embodiments, the present invention provides methods comprising administering the foregoing compositions to a companion animal in an amount effective for improving atopic and pruritic skin conditions in companion animals. In some embodiments, the present invention provides methods comprising administering the foregoing compositions to a companion animal in an amount effective for improving various skin problems in a companion animal including dry skin, excessive shedding, pruritus, pyotraumatic dermatitis and furunculosis. In some embodiments, the present invention provides methods comprising administering the foregoing compositions to a companion animal in an amount effective for improving paw pads. In some embodiments, the present invention provides methods comprising administering the foregoing compositions to a companion animal in an amount effective for reducing the discoloration of the coat/fur. In some embodiments, the foregoing compositions are provided for use in improving atopic and pruritic skin conditions in companion animals, improving various skin problems in a companion animal including dry skin, excessive shedding, pruritus, pyotraumatic dermatitis and furunculosis, or improving paw pads.

In some embodiments, the present invention provides lipid compositions comprising linoleic acid (LA), alpha-linolenic acid (ALA), stearidonic acid (SDA) and gamma linolenic acid (GLA), said LA and ALA in a ratio of about less than 2:1 LA:ALA. In some embodiments, the ratio of LA:ALA is from about 1.99:1 to about 0.5:1. In some embodiments, the amounts of the fatty acids are determined by gas chromatography, while in other embodiments, the amounts of fatty acids are determined by mass spectrometry. In some embodiments, the lipid composition comprises greater than about 1%, 2% or 3% to about 5% or 10% SDA and GLA as determined by gas chromatography. In some embodiments, the amount of GLA to SDA is at least 2:1. In some embodiments, the ratio of LA to GLA is at least 10:1 and the ratio of ALA to SDA is at least 10:1 as determined by gas chromatography. In some embodiments, the ratio of LA to GLA is at least 20:1 and the ratio of ALA to SDA is at least 20:1 as determined by gas chromatography. In some embodiments, the LA, ALA, GLA and SDA are obtained from linseed oil, rapeseed oil and hempseed oil. In some embodiments, the compositions further comprise a mixture of natural or synthetic tocopherols (α, β, γ, δ). In some embodiments, the compositions are essentially free of EPA and DHA. In some embodiments, the LA, ALA, GLA and SDA are obtained the group consisting of oil seed press cakes including linseed, hempseed and camelina seed as well as linseed oil, full fat linseeds, hempseed oil and full fat hemp seed. In some embodiments, the present invention provides a lipid mixture comprising LA and ALA in a ratio of less than 2:1 and GLA and SDA in a ratio of 2:1 effective on alleviating skin problems in companion animals.

In some embodiments, the present invention provides methods comprising administering compositions as described above in an amount effective to improve, treat, or prevent one or more conditions of the skin, paws or hair of an animal, such as a companion animal. In some embodiments, the condition is selected from the group consisting of: eczema, dry skin, flaky skin, pruritus, pyotraumatic dermatitis, furunculosis, dry paw pads, rough paw pads, chapped paw pads, paw pad durability, dry rhinarium, chapped rhinarium, split claws, brittle claws, rashes, hairless spots, hot spots, symmetrical lupoid onychodystrophy, skin ulceration, skin crusting, reddening of skin between toes, external ear infection, and nutritional dermatosis. In some embodiments, the companion animal is selected from the group consisting of a dog, cat, horse, rabbit, rat, mouse, hamster, guinea pig and gerbil. In some embodiments, the compositions are delivered in an amount effective for improving the skin, hair or paw pads of said animal.

In some embodiments, the compositions described above are provided for use to improve, treat, or prevent one or more conditions of the skin, paws or hair of an animal, such as a companion animal. In some embodiments, the compositions are provided for use in improving atopic and pruritic skin conditions in companion animals or improving conditions in a companion animal selected from the group consisting of eczema, dry skin, flaky skin, pruritus, pyotraumatic dermatitis, furunculosis, dry paw pads, rough paw pads, chapped paw pads, paw pad durability, dry rhinarium, chapped rhinarium, split claws, brittle claws, rashes, hairless spots, hot spots, symmetrical lupoid onychodystrophy, skin ulceration, skin crusting, reddening of skin between toes, external ear infection, and nutritional dermatosis.

DEFINITIONS

As used herein, the term omega-3 fatty acid refers to polyunsaturated fatty acids that have the final double bond in the hydrocarbon chain between the third and fourth carbon atoms from the methyl end of the molecule. Non-limiting examples of omega-3 fatty acids include, all-cis-9,12,15-octadecatrienoic acid (alpha-linolenic acid or ALA), all-cis-5,8,11,14, 17-eicosapentaenoic acid (EPA), all-cis-4,7,10,13,16,19-docosahexanoic acid (DHA) and all-cis 6,9,12,15-octadecatetraenoic acid (stearidonic acid or SDA).

As used herein, the term omega-6 fatty acid refers to polyunsaturated fatty acids that have the final double bond in the hydrocarbon chain between the sixth and seventh carbon atoms from the methyl end of the molecule. Non-limiting examples of omega-6 fatty acids include, all-cis-6,9,12-octadecatrienoic acid (gamma-linolenic acid or GLA) and all-cis-9,12-octadecadienoic acid (linoleic acid or LA).

DETAILED DESCRIPTION OF THE INVENTION

Figure 1:
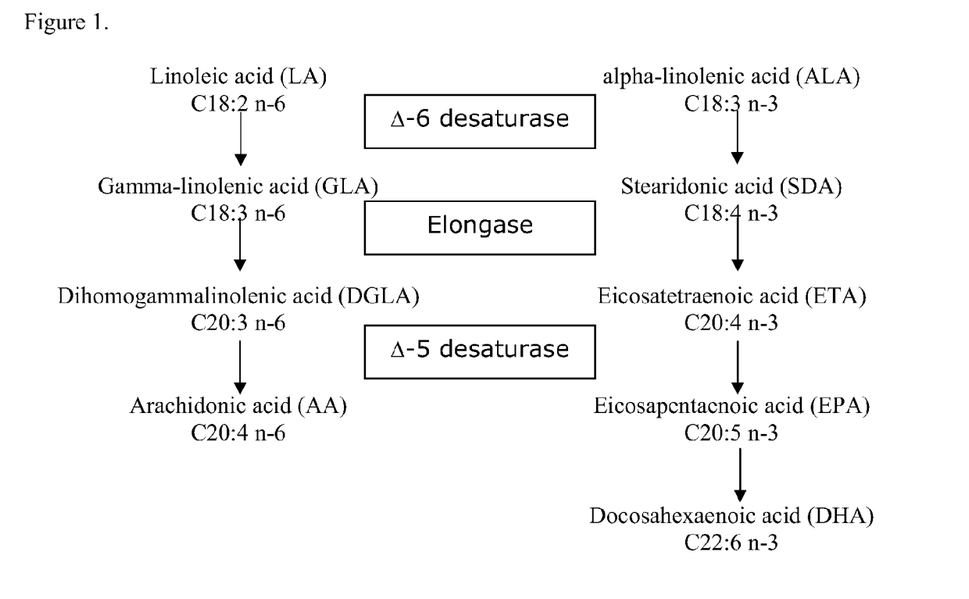
FIG. 1. Metabolism of essential fatty acids, LA and ALA, and identification of their immediate products GLA and SDA.

Linoleic acid (LA) and alpha-linolenic acid (ALA) are considered to be essential fatty acids for animals, because they are not synthesized in the body and therefore are required to be obtained through the diet. Gamma-linolenic acid (GLA) and stearidonic acid (SDA) are the immediate metabolites of LA and ALA, respectively (FIG. 1). Previously, a clinical study data was published showing that dietary supplementation with hempseed oil characterized by its content of LA, ALA, SDA and GLA should be effective in treating atopic dermatitis in humans. Similar to humans, companion animals such as dogs and cats suffer from various skin problems, but due to the differences in physiology e.g. activity of enzymes that metabolize essential fatty acids in the skin, Δ5- and Δ6-desaturase, it is not obvious whether the fatty acid mixture shown to be biologically effective in humans would be biologically active also in dogs and cats. A dietary strategy to treat various skin problems in companion animals is very much in need, because of the high incidence of problems of the skin and paw pad problems. However, there is paucity of information regarding bio-effective lipid compositions. This invention discloses results from several clinical cases with dogs, horses and cats showing that a mixture of hempseed oil, rapeseed oil and linseed oil is effective in a ratio of 50:45:5 (v/v/v). In some embodiments, the lipid compositions are characterized by having a LA:ALA ratio of at least 2:1 and a GLA:SDA ratio of at least 2:1. In some embodiments, the lipid mixture is characterized by having a LA:GLA ratio of 17:1 and ALA:SDA ratio of 18:1. In some embodiments, the lipid mixtures have ratios of LA:GLA and ALA:SDA ratio of 10:1.

In some preferred embodiments, the present invention provides lipid compositions comprising hempseed oil, linseed oil and rapeseed oil. In some embodiments, the oils have been mixed in proportions that give LA:ALA ratio of at least 2:1 and the GLA:SDA ratio of at least 2:1. In some embodiments, the oil compositions have a ratio of LA:GLA of up to 20:1 and a ratio of ALA:SDA of up to 20:1. In some embodiments, the oils can also be mixed in proportions that give LA:ALA ratio less than 2:1 (e.g. 1.9:1 to 1.99:1). In some embodiments, the oil compositions have LA:ALA ratios from about 1.5:1 to about 2.39:1. In some embodiments, the lipid compositions contain GLA+SDA at the level at least 3% of total fatty acids. The lipid compositions of the present invention have novel biological properties in the area of improved skin conditions in companion animals.

In some embodiments, these fatty acid ratios are obtained by mixing oils from different sources containing LA, ALA, GLA and SDA. Non-limiting sources of these fatty acids are rapeseed oil, linseed oil, sunflower oil, soybean oil, rice bran oil, corn oil, almond oil to supply LA and ALA and hempseed oil, evening primrose oil, borage oil, echium oil and black-currant seed oil to supply GLA and SDA. Also oils with enriched levels of GLA and SDA from genetically modified oil seed crops such as canola and soybean can be used in the formulation. The composition disclosed comprised of appreciable amounts of rapeseed oil. Rapeseed oil contains LA and ALA in 2 to 1 ratio, but it is essentially devoid of GLA and SDA. By adding rapeseed oil, oleic acid could be added into the formulation without introducing a deviation from the desired balance between essential fatty acids. Another embodiment of this invention is to include a mixture of natural d-tocopherols ($\alpha$, $\beta$, $\gamma$ and $\delta$) in the oil blend. Tocopherols are used in the oil blend for antioxidant protection, but they may also contribute to the observed skin health effects.

In some embodiments, the compositions of this invention are contained in acceptable excipients and/or carriers for oral consumption. The actual form of the carrier, and thus, the compositions itself, is not critical. The carrier may be a liquid, gel, gelcap, capsule, powder, solid tablet (coated or non-coated), tea, or the like. The composition is preferably in the form of a tablet or capsule and most preferably in the form of a hard gelatin capsule. Suitable excipient and/or carriers include maltodextrin, calcium carbonate, dicalcium phosphate, tricalcium phosphate, microcrystalline cellulose, dextrose, rice flour, magnesium stearate, stearic acid, croscarmellose sodium, sodium starch glycolate, crospovidone, sucrose, vegetable gums, lactose, methylcellulose, povidone, carboxymethylcellulose, corn starch, and the like (including mixtures thereof). Preferred carriers include calcium carbonate, magnesium stearate, maltodextrin, and mixtures thereof. The various ingredients and the excipient and/or carrier are mixed and formed into the desired form using conventional techniques. The tablet or capsule of the present invention may be coated with an enteric coating that dissolves at a pH of about 6.0 to 7.0. A suitable enteric coating that dissolves in the small intestine but not in the stomach is cellulose acetate phthalate. Further details on techniques for formulation for and administration may be found in the latest edition of *Remington's Pharmaceutical Sciences* (Mack Publishing Co., Easton, Pa.). In other embodiments, the composition contains no traces of organic solvents which is an important property regarding the safety of consuming such compounds.

In other embodiments, the supplement is provided as a powder or liquid suitable for adding by the consumer to a food or beverage. For example, in some embodiments, the dietary supplement can be administered to an individual in the form of a powder, for instance to be used by mixing into a beverage, or by stirring into a semi-solid food such as a pudding, topping, sauce, puree, cooked cereal, or salad dressing, for instance, or by otherwise adding to a food.

The compositions of the present invention may also be formulated with a number of other compounds. These compounds and substances add to the palatability or sensory perception of the particles (e.g., flavorings and colorings) or improve the nutritional value of the particles (e.g., minerals, vitamins, phytonutrients, antioxidants, etc.).

The dietary supplement may comprise one or more inert ingredients, especially if it is desirable to limit the number of calories added to the diet by the dietary supplement. For example, the dietary supplement of the present invention may also contain optional ingredients including, for example, herbs, vitamins, minerals, enhancers, colorants, sweeteners, flavorants, inert ingredients, and the like. For example, the dietary supplement of the present invention may contain one or more of the following: ascorbates (ascorbic acid, mineral ascorbate salts, rose hips, acerola, and the like), dehydroepiandosterone (DHEA), Fo-Ti or Ho Shu Wu (herb common to traditional Asian treatments), Cat's Claw (ancient herbal ingredient), green tea (polyphenols), inositol, kelp, dulse, bioflavinoids, maltodextrin, nettles, niacin, niacinamide, rosemary, selenium, silica (silicon dioxide, silica gel, horsetail, shavegrass, and the like), spirulina, zinc, and the like. Such optional ingredients may be either naturally occurring or concentrated forms.

In some embodiments, the dietary supplements further comprise vitamins and minerals including, but not limited to, calcium phosphate or acetate, tribasic; potassium phosphate, dibasic; magnesium sulfate or oxide; salt (sodium chloride); potassium chloride or acetate; ascorbic acid; ferric orthophosphate; niacinamide; zinc sulfate or oxide; calcium pantothenate; copper gluconate; riboflavin; beta-carotene; pyridoxine hydrochloride; thiamin mononitrate; folic acid; biotin; chromium chloride or picolonate; potassium iodide; sodium selenate; sodium molybdate; phylloquinone; vitamin $D_3$; cyanocobalamin; sodium selenite; copper sulfate; vitamin A; vitamin C; inositol; potassium iodide. Suitable dosages for vitamins and minerals may be obtained, for example, by consulting the U.S. RDA guidelines.

In further embodiments, the compositions comprise at least one food flavoring such as acetaldehyde (ethanal), acetoin (acetyl methylcarbinol), anethole (parapropenyl anisole), benzaldehyde (benzoic aldehyde), N-butyric acid (butanoic acid), d- or l-carvone (carvol), cinnamaldehyde (cinnamic aldehyde), citral (2,6-dimethyloctadien-2,6-al-8, geranial, neral), decanal (N-decylaldehyde, capraldehyde, capric aldehyde, caprinaldehyde, aldehyde C-10), ethyl acetate, ethyl butyrate, 3-methyl-3-phenyl glycidic acid ethyl ester (ethyl-methyl-phenyl-glycidate, strawberry aldehyde, C-16 aldehyde), ethyl vanillin, geraniol (3,7-dimethyl-2,6 and 3,6-octadien-1-ol), geranyl acetate (geraniol acetate), limonene (d-, l-, and dl-), linalool (linalol, 3,7-dimethyl-1,6-octadien-3-ol), linalyl acetate (bergamol), methyl anthranilate (methyl-2-aminobenzoate), piperonal (3,4-methylenedioxy-benzaldehyde, heliotropin), vanillin, alfalfa (*Medicago sativa* L.), allspice (*Pimenta officinalis*), ambrette seed (*Hibiscus abelmoschus*), angelic (*Angelica archangelica*), Angostura (*Galipea officinalis*), anise (*Pimpinella anisum*), star anise (*Illicium verum*), balm (*Melissa officinalis*), basil (*Ocimum basilicum*), bay (*Laurus nobilis*), calendula (*Calendula officinalis*), (*Anthemis nobilis*), capsicum (*Capsicum frutescens*), caraway (*Carum carvi*), cardamom (*Elettaria cardamomum*), cassia, (*Cinnamomum cassia*), cayenne pepper (*Capsicum frutescens*), Celery seed (*Apium graveolens*), chervil (*Anthriscus cerefolium*), chives (*Allium schoenoprasum*), coriander (*Coriandrum sativum*), cumin (*Cuminum cyminum*), elder flowers (*Sambucus canadensis*), fennel (*Foeniculum vulgare*), fenugreek (*Trigonella foenum-graecum*), ginger (*Zingiber officinale*), horehound (*Marrubium vulgare*), horseradish (*Armoracia lapathifolia*), hyssop (*Hyssopus officinalis*), lavender (*Lavandula officinalis*), mace (*Myristica fragrans*), marjoram (*Majorana hortensis*), mustard (*Brassica nigra, Brassica juncea, Brassica hirta*), nutmeg (*Myristica fragrans*), paprika (*Capsicum annuum*), black pepper (*Piper nigrum*), peppermint (*Mentha piperita*), poppy seed (*Papayer somniferum*), rosemary (*Rosmarinus officinalis*), saffron (*Crocus sativus*), sage (*Salvia officinalis*), savory (*Satureia hortensis, Satureia montana*), sesame (*Sesamum indicum*), spearmint (*Mentha spicata*), tarragon (*Artemisia dracunculus*), thyme (*Thymus vulgaris, Thymus serpyllum*), turmeric (*Curcuma longa*), vanilla (*Vanilla planifolia*), zedoary (*Curcuma zedoaria*), sucrose, glucose, saccharin, sorbitol, mannitol, aspartame. Other suitable flavoring are disclosed in such references as Remington's Pharmaceutical Sciences, 18th Edition, Mack Publishing, p. 1288-1300 (1990), and Furia and Pellanca, Fenaroli's Handbook of Flavor Ingredients, The Chemical Rubber Company, Cleveland, Ohio, (1971), known to those skilled in the art.

In other embodiments, the compositions comprise at least one synthetic or natural food coloring (e.g., annatto extract, astaxanthin, beet powder, ultramarine blue, canthaxanthin, caramel, carotenal, beta carotene, carmine, toasted cottonseed flour, ferrous gluconate, ferrous lactate, grape color extract, grape skin extract, iron oxide, fruit juice, vegetable juice, dried algae meal, tagetes meal, carrot oil, corn endosperm oil, paprika, paprika oleoresin, riboflavin, saffron, tumeric, tumeric and oleoresin).

In still further embodiments, the compositions comprise at least one phytonutrient (e.g., soy isoflavonoids, oligomeric proanthcyanidins, indol-3-carbinol, sulforaphone, fibrous ligands, plant phytosterols, ferulic acid, anthocyanocides, triterpenes, conjugated fatty acids such as conjugated linoleic acid and conjugated linolenic acid, polyacetylene, quinones, terpenes, cathechins, gallates, and quercitin). Sources of plant phytonutrients include, but are not limited to, soy lecithin, soy isoflavones, brown rice germ, royal jelly, bee propolis, acerola berry juice powder, Japanese green tea, grape seed extract, grape skin extract, carrot juice, bilberry, flaxseed meal, bee pollen, *ginkgo biloba*, red clover, burdock root, dandelion, parsley, rose hips, milk thistle, ginger, Siberian ginseng, rosemary, curcumin, garlic, lycopene, grapefruit seed extract, spinach, and broccoli.

In still other embodiments, the compositions comprise at least one vitamin (e.g., vitamin A, thiamin (B1), riboflavin (B2), pyridoxine (B6), cyanocobalamin (B12), biotin, ascorbic acid (vitamin C), retinoic acid (vitamin D), vitamin E, folic acid and other folates, vitamin K, niacin, and pantothenic acid). In some embodiments, the particles comprise at least one mineral (e.g., sodium, potassium, magnesium, calcium, phosphorus, chlorine, iron, zinc, manganese, fluorine, copper, molybdenum, chromium, selenium, and iodine). In some particularly preferred embodiments, a dosage of a plurality of particles includes vitamins or minerals in the range of the recommended daily allowance (RDA) as specified by the United States Department of Agriculture. In still other embodiments, the particles comprise an amino acid supplement formula in which at least one amino acid is included (e.g., 1-carnitine or tryptophan).

In some embodiments, the lipid compositions of the present invention find use in treating skin conditions in companion animals such as dogs, cats and horses. Dogs with white hair coat often develop a yellowish/brownish taint. The reason is not clear, but could be due to imbalanced nutrition. This discoloration is obviously not wanted, especially not for show animals. An improvement of the white hair coat could be obtained for subjects with a discoloured hair coat by using the disclosed lipid composition. Furthermore, this invention discloses that the lipid composition was effective in treating various skin conditions such as dry skin, excessive shedding, pruritus, pyotraumatic dermatitis and furunculosis in dogs. In addition, the composition disclosed was highly effective in improving the skin in the dog's paw pads. Dietary supplementation with the disclosed oil composition has improved the appearance of the hair coat in cats and provided relief for horses suffering from 'summer eczema'. Furthermore, this invention discloses that the ratios of the fatty acids are important in order to observe the biological effect on the skin in dogs and other companion animals. A composition comprising LA and ALA in 2:1 ratio, but no GLA and SDA was not effective in treating skin problems in dogs. Currently there are products available on the market where the bioactive component is GLA or the bioactive component consists of a mixture of GLA and fish oil derived fatty acids EPA and DHA. Long chain omega-3 fatty acid such as EPA and DHA is considered to enhance the GLA effect in fatty acid formulations [7]. Products containing fish oil derived fatty acids are not desirable since number of dogs are allergic to fish protein and therefore should not be given products that contain fish oil or fish oil derived fatty acids. This invention discloses that a highly effective nutritional oil blend could be formulated without using any EPA or DHA in the blend.

In addition, this invention further discloses a formulation that has an improved stability and increased shelf life compared to cold pressed plant oils such as hempseed oil or oil blends consisting of cold pressed oils. A further improvement in the stability of the oil blend could be obtained by using refined oils compared to cold pressed oils. The use of cold pressed plant oils results in shelf life limited to 6 to 12 months. This is due to the presence of materials in cold pressed oils that reduce the stability of the oils. This invention discloses the use of refined plant oils and thereby also extended shelf life.

Horses have frequently been observed with skin problems such as summer eczema. The cost of hemp seed oil is high and due to the size of the horse a large dose is required in order to induce a therapeutic effect. Hence a treatment strategy based on hemp seed oil is likely to become prohibitively expensive. During hempseed oil production a hemp seed press cake is obtained as a by-product. This press cake consists of up to 17% residual oil and significant amounts of protein of good quality. Oily formulation containing hemp seed oil has to be kept in the refrigerator to prevent oxidation, whereas hemp seed press cake is a stable product up to 2 years. In yet another embodiment of this invention is a product particularly useful for feeding horses. In order to provide the beneficial skin health effects of the specific fatty acid ratios as described above, by-products of oilseed pressing i.e. press cakes are used. Alternatively are ground/crushed full fat oilseeds used or mixtures of press cake and full fat oilseeds in order to make the final product.

EXAMPLE 1

Hempseed oil (made from Finola variety of seeds), rapeseed oil and linseed oil were mixed in approximately 50:45:5 (v/v/v) ratio. This oil blend was homogenized and a mixture of natural d-tocopherols—β, β, γ, δ (Coviox T-70) was added to the mixture at 2000 μg/g of oil. The fatty acid profile was determined using GC-FID and tocopherols using NP-HPLC with fluorescence detection. The results are listed in table 1. Listed in table 2 is the typical fatty acid profile of the individual oils used to prepare the novel lipid mixture in this example.

TABLE 1

Major fatty acids and tocopherols in the nutritional oil blend

| Fatty acids, % of total fatty acids | |
|---|---|
| 16:0 | 4.4 |
| 18:0 | 2.0 |
| 18:1 (n-9) | 29.3 |
| 18:2 (n-6); LA | 34.3 |
| 18:3 (n-6); GLA | 2.0 |
| 18:3 (n-3); ALA | 17.8 |
| 18:4 (n-3); SDA | 1.0 |
| LA:ALA | 2:1 |
| GLA:SDA | 2:1 |
| LA:GLA | 17:1 |
| ALA:SDA | 18:1 |

TABLE 1-continued

Major fatty acids and tocopherols in the nutritional oil blend

Tocopherols, µg/g

| | |
|---|---|
| α-tocopherol | 405 |
| β-tocopherol | 40 |
| γ-tocopherol | 1812 |
| δ-tocopherol | 511 |
| TOTAL | 2769 |

TABLE 2

Fatty acid profiles of the individual oils used in example 1.

| | Hemp seed oil[1] | Rapeseed oil | Linseed oil |
|---|---|---|---|
| Fatty acids, % of total fatty acids | | | |
| 16:0 | 6.4 | — | 6.0 |
| 18:0 | 2.4 | 7.0 | 2.5 |
| 18:1 (n-9) | 8.3 | 54.0 | 19.0 |
| 18:2 (n-6); LA | 55.1 | 30.0 | 14.0 |
| 18:3 (n-6); GLA | 4.6 | — | — |
| 18:3 (n-3); ALA | 19.7 | 7.0 | 58.0 |
| 18:4 (n-3); SDA | 1.7 | — | — |
| Tocopherols, µg/g | | | |
| α-tocopherol | 51 | 220 | 12 |
| β-tocopherol | — | | |
| γ-tocopherol | 839 | 370 | 520 |
| δ-tocopherol | 44 | 19 | 10 |
| TOTAL | 934 | 609 | 544 |

[1]Finola variety of hempseed

EXAMPLE 2

A placebo controlled, double blind study was performed using 91 dogs living with their owners. Recruited dogs were of different breeds and considered to be without any apparent skin problems. Duration of the study was 8 weeks with control visits by the researcher at the start of the study, half way through the study and in the end of the study. The dogs were administered either placebo (rapeseed oil) or test oil (nutritional oil blend) at 4 ml/10 kg of body weight on top of their normal diet. Only dogs that did not use any other oil supplements were recruited. Owners of the dogs were given questionnaires which they filled in at each control visit. The purpose of the study was to examine the safety and tolerability of a nutritional oil blend as prepared in example 1 in comparison to rapeseed oil placebo. Rapeseed oil contains LA and ALA in 2:1 ratio and it is essentially devoid of GLA and SDA. As described in table 1, nutritional oil blend contained LA and ALA as well as GLA and SDA in 2:1 ratio, respectively. The study demonstrated that the nutritional oil blend was well tolerated without any adverse effects. Thus, in terms of safety and tolerability it did not distinguish from the rapeseed oil placebo. Detailed analysis of the study questionnaires revealed that a number of dogs with minor skin and coat problems (shedding, pruritus, desquamation, dull hair coat and dry paw pads) were included in the test oil group of the study population. Examination of the responses of the dogs with minor skin and coat problems revealed that the test material provided some alleviation of the skin problems in 8 out of 10 cases. This result indicates that the nutritional oil blend characterized by specific ratios of essential fatty acids and their immediate precursors and antioxidants is effective alleviating minor skin problems.

EXAMPLE 3

Dogs with white hair coat often develop a yellowish/brownish taint. The inherent reason for the discolouring is not known, but there could be an association with diet. In show dogs, the discolouring is obviously not a desirable characteristic. A litter of six puppies of White Shepherds was divided in two groups at the time of weaning. Three puppies were supplemented daily with the nutritional oil blend as prepared in example 1 and followed for six months of age. At this age it was evident that the three dogs supplemented with the nutritional oil blend had much whiter hair coat than the three puppies that were fed a standard dog chow containing sufficient amounts of essential fatty acids without any oil supplementation.

EXAMPLE 4

When dog paw pads are too dry and chapped they can become more easily injured than paw pads that are smooth and supple. A study was performed with 10 dogs recruited by a professional groomer. These dogs all had suffered from extremely dry and chapped paw pads for extended periods of time. On a scale from 1 to 4 where 1 is smooth and 4 is extremely rough and chapped, the dogs averaged 3.6. The diet of the dogs at the start of the study was analyzed and found to contain sufficient amounts of essential fatty acids, LA and ALA. In some cases the LA to ALA ratio in the diet was as high as 20:1. All the dog owners were given instructions to supplement their dogs daily with the nutritional oil blend as prepared in example 1 at 4 ml/10 kg for three months. After six weeks, each dog was examined and the condition of the paw pads was scored. In all dogs the condition of the paw pad had improved (Table 3). Further and consistent improvement in the paw pad condition in the study population was observed after 12 weeks of the study (Table 3). At this point the average roughness score in the study population was 1.7. These results indicate that the nutritional oil blend characterized by specific ratios of essential fatty acids and their immediate precursors and antioxidants is effective in improving the condition of dog paw pads when administered as a supplement on top of the normal diet which contains sufficient amount of essential fatty acids.

TABLE 3

Change in the dog paw pad condition during a 12 week dietary supplementation with the nutritional oil.

| | Roughness score | | | |
|---|---|---|---|---|
| | 1 | 2 | 3 | 4 |
| Start | — | — | 4 | 6 |
| 6 weeks | 1 | 4 | 4 | 1 |
| 12 weeks | 4 | 5 | 1 | — |

Number of dogs in each class of roughness score. Scoring: 1 = smooth, 4 = extremely rough and chapped.

EXAMPLE 5

A twelve-year old male Labrador retriever had suffered for many years from various skin problems including dry skin, excessive shedding, pruritus, pyotraumatic dermatitis, furunculosis and mild parakeratosis of the nose. The dog had been treated several times a year by the veterinarian and medicated with antibiotics, cortisone, ointments etc. The dog also received nutritional supplements containing GLA and EPA.

In spite of the medical and nutritional treatments the skin problems persisted and the severe skin problems like the pyotraumatic dermatitis reoccurred multiple times. When this dog was given a nutritional oil blend as prepared in example 1 at 4 ml/10 kg the skin condition gradually improved with all the symptoms gone after 2 months. Continuous supplementation with the oil blend allowed the dog to maintain a healthy skin. Both pyotraumatic dermatitis and furunculosis are bacterial diseases. This example does not suggest that the nutritional oil blend in example 1 has antibacterial activity, but it may indicate that dogs predisposed to bacterial infections of the skin could be protected from the infections by targeted use of nutrients present in the nutritional oil blend.

EXAMPLE 6

An eight-year-old Parson Russell terrier had suffered for a long time from atopic and pruritic skin. The dog had been treated with cortisone and with a variety of different fatty acid supplements containing GLA and fish oil fatty acids (EPA and DHA). These treatments provided help only for some weeks. Constant itching tired the dog and it became phlegmatic. The dog was put on daily dosing of the nutritional oil blend as prepared in example 1 and a clear change in the dogs skin condition and behaviour occurred in a matter of weeks. The rashes and itching was reduced by 95%. This case indicates that the nutritional oil blend is effective in alleviating atopic skin condition.

EXAMPLE 7

Dogs with exocrine pancreatic insufficiency (EPI) suffer from nutrient malabsorption and develop chronic skin problems due to essential fatty acid deficiency. Supplementation with oils containing essential fatty acids is a standard treatment although supplementation with oil in these dogs can lead to diarrhoea and steatorrhea. A three-year-old German shepherd with EPI demonstrated the classic symptoms of essential fatty acid deficiency of dull hair coat and dry skin that could not be controlled by diet or fatty acid supplements. Administration of the oil blend as prepared in example 1 at 4 ml/20 kg (50% of the recommended dose) for 2 months resulted in alleviation of the skin problems: hair coat became shiny and excessive shedding ceased. This example demonstrates that the nutritional oil blend as prepared in example 1 is well tolerated by dogs with EPI and effective in alleviating skin problems at 50% of the recommended dose.

EXAMPLE 8

Summer eczema (SE) also known as equine insect bite hypersensitivity or sweet itch, is a chronic, recurrent seasonal dermatitis of horses caused by an allergic reaction to the bite of *Culicoides* ssp (biting midge). The symptoms include intense pruritus, self-excoriation resulting in open wounds and secondary infections and are usually localized to the mane, tail and withers. Prevalence of SE is particularly high in Icelandic horses. According to Björnsdottir et al. [13] 35% of Icenlandic horses living outside of Iceland are inflicted with this condition. A group of 3 Icelandic horses with recurring SE was treated with the nutritional oil blend as prepared in example 1 at 12.5 ml/100 kg body weight at the time the first symptoms of SE occurred. Use of the nutritional oil alleviated the initial symptoms and prevented the aggravation of SE. This example demonstrates that the nutritional oil can reduce the hypersensitivity reaction to the biting midge in horses.

EXAMPLE 9

Figure 2:
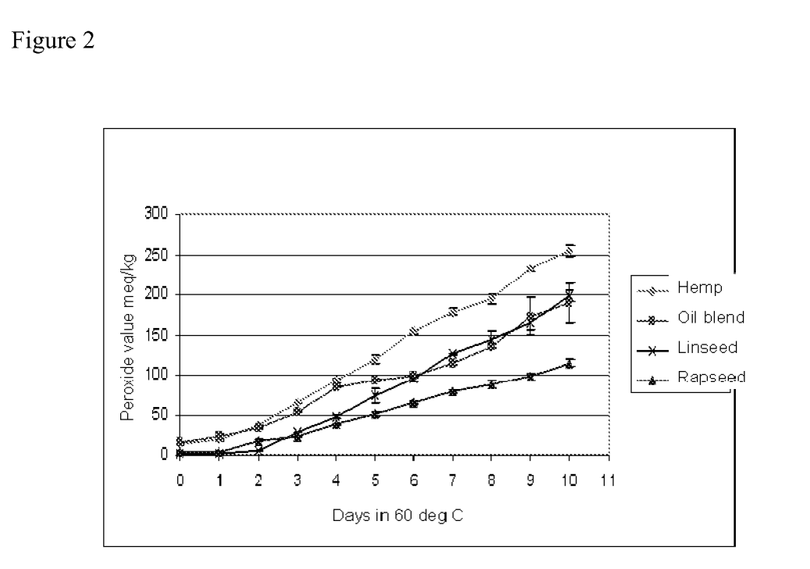
FIG. 2. Oxidative stability of the nutritional oil blend and its components incubated at 60° C. for two weeks. Stability measured as peroxide value.

An accelerated oxidative stability test was performed as follows: samples of the nutritional oil blend in example 1 and its component oils, hempseed oil, rapeseed oil and linseed oil, were kept in 60° C. for 10 days and the levels of lipid peroxides (peroxide value; PV) were determined daily. In all cases the PV increased over time (FIG. 2) with the most pronounced increase in hempseed oil and least increase in rapeseed oil with intermediate increase in linseed oil and in the oil blend of example 1. This example demonstrates that blending hempseed oil rapeseed oil and linseed oil in 50:45:5 ratio and including and addition of natural tocopherols (Coviox T-70; at 2 mg/g of oil) results in a better oxidative stability in the blend compared to hempseed oil.

EXAMPLE 10

Figure 3:
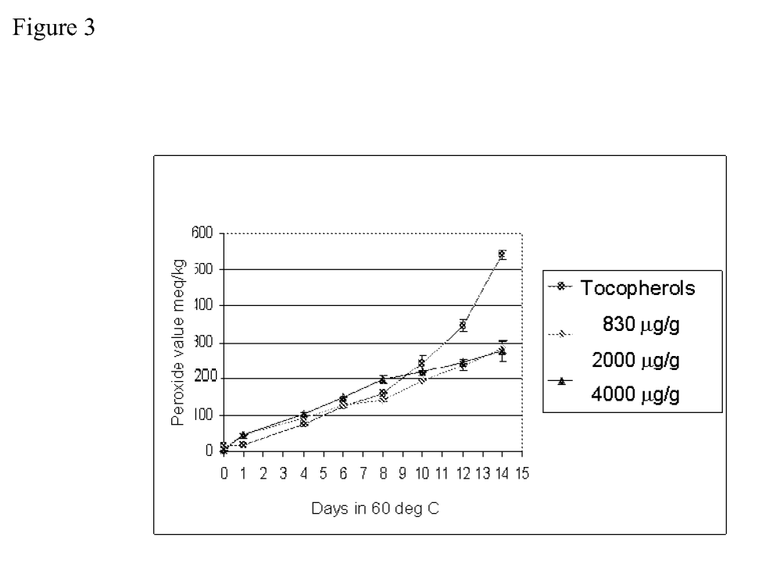
FIG. 3. Oxidative stability of the nutritional oil blend containing natural tocopherols at three different inclusion levels incubated at 60° C. for 2 weeks. Stability measured as peroxide value.

Addition of mixed tocopherols at 2000 µg/g into the oil blend (Example 1) improves the stability of the oil blend (FIG. 3). High levels of tocopherols can potentially introduce a pro-oxidative effect in the oil blend. Addition of tocopherols at 4000 µg/g into the oil blend was tested and it was found that this level of tocopherols in the oil did not influence the oxidative stability of the oil blend. This example shows that the tocopherol content of the oil blend can be further increased to 4000 µg/g without any adverse effect on the oxidative stability of the oil blend.

EXAMPLE 11

According to the distributor of Finola° hempseed oil, Elixi Oil Ltd (Somero, Finland) the oil should be stored in refrigerated conditions to prevent oxidation. This is not practical in most commercial situations. Against this background the oxidative stability of the nutritional oil blend was determined once a month in oil blend samples kept in room temperature by measuring the peroxide value (PV). In six months, PV increased from 5 to 7 meq/kg which does not indicate increased level of oxidation, but it indicates that the level of peroxides is acceptable for nutritional oils intended for use in companion animals.

EXAMPLE 12

An accelerated oxidative stability test is to be performed at 60° C. In this test the nutritional oil blend based on cold pressed plant oils is compared with a nutritional oil blend consisting of refined plant oils with identical ratios between LA:ALA, GLA:SDA, LA:GLA and ALA:SDA. It is to be found that the nutritional oil blend consisting of refined plant oils demonstrates a more gradual increase in peroxide value suggesting that this oil blend is more stable than the oil blend based on cold pressed plant oils. It can also be demonstrated with an in vivo test that the efficacy of the nutritional oil blend based on refined plant oils is equal to the one based on cold pressed oils.

EXAMPLE 13

The essential fatty acid (LA:ALA) and the immediate metabolite (GLA:SDA) ratios as described for example 1 can be produced by blending variety of natural oils containing LA, ALA, GLA and SDA. Examples of oil blends producing desired fatty acid ratios presented in Table 4.

TABLE 4

Examples of oil blends that have the same essential fatty acid and immediate metabolite ratios as the nutritional oil blend as described in example 1

|  | Blend a | Blend b | Blend c | Blend d |
|---|---|---|---|---|
| Soybean oil | 0.56 | — | — | — |
| Safflower oil | — | 0.50 | — | — |
| Sunflower oil | — | — | 0.54 | 0.46 |
| Evening primrose oil | 0.11 | — | — | — |
| Borage oil | — | 0.06 | — | — |
| *Echium plantagineum* | 0.09 | 0.09 | — | — |
| GMO canola oil | — | — | 0.045 | 0.09 |
| GMO soybean oil | — | — | 0.06 | 0.12 |
| Linseed oil | 0.24 | 0.35 | 0.35 | 0.33 |
| TOTAL | 1.00 | 1.00 | 1.00 | 1.00 |
| Fatty acids | | | | |
| 16:0 | 7.7 | 3.3 | 3.1 | 3.8 |
| 18:0 | 4.4 | 7.3 | 7.8 | 7.2 |
| 18:1 (n-9) | 21.0 | 15.3 | 21.3 | 21.0 |
| 18:2 (n-6); LA | 41.6 | 46.7 | 43.2 | 40.6 |
| 18:3 (n-6); GLA | 2.0 | 2.2 | 2.0 | 4.0 |
| 18:3 (n-3); ALA | 20.8 | 23.3 | 21.6 | 20.5 |
| 18:4 (n-3); SDA | 1.0 | 1.1 | 1.0 | 2.0 |
| LA:ALA | 2:1 | 2:1 | 2:1 | 2:1 |
| GLA:SDA | 2:1 | 2:1 | 2:1 | 2:1 |
| LA:GLA | 20:1 | 20:1 | 20:1 | 10:1 |
| ALA:SDA | 20:1 | 20:1 | 20:1 | 10:1 |

EXAMPLE 14

A safety and tolerability study was performed in human subjects. Five healthy individuals with symptoms of dry and itchy skin were recruited in the study and supplemented with the nutritional oil blend prepared as in example 1 for six weeks. The dosage was determined relative to body surface area. For example a person weighing 56 kg took a daily dose of 16 ml of oil and a person weighing 68 kg took a daily dose of 18 ml. Nutritional oil blend was safe and well tolerated among healthy individuals. Thus the nutritional oil blend can be used as a dietary supplement.

EXAMPLE 15

A feed product comprising of hempseed press cake, linseed press cake, linseed oil, starch, molasses and 2000 μg/g of oil natural d-tocopherols—α, β, γ, δ (Coviox T-70) is to be made as shown (Table 5 shows the composition of the feed). The feed product is to be fed to a horse weighing about 500 kg and having dry, flaky skin and dull hair coat. It is to be observed an improvement in the skin condition after feeding an effective amount of the feed product to the horse. It is to be shown that the effective dose of oil providing beneficial effects on the skin for a 500 kg horse is estimated to contain 40 to 45 g of oil derived from hempseed and linseed. The oil content of hempseed press cake is to be about 17% and the oil content in linseed press cake is to be about 17%. Some linseed oil is to be added to the feed to increase the ratio of LA and ALA to 2:1.

TABLE 5

Composition of the feed product made in Example 15 comprising press cakes and oil.

| Contents | g/kg |
|---|---|
| Hempseed press cake | 740 |
| Linseed press cake | 80 |

TABLE 5-continued

Composition of the feed product made in Example 15 comprising press cakes and oil.

| Contents | g/kg |
|---|---|
| Linseed oil | 5 |
| Source of starch (grain) | 125 |
| Molasses | 50 |
| Mixed tocopherols, μg/g of oil | 2000 |

EXAMPLE 16

A feed product comprising of ground full fat hempseed, hempseed press cake, linseed press cake, linseed oil, starch, molasses and 2000 μg/g of oil natural d-tocopherols—α, β, γ, δ (Coviox T-70) is to be made as shown (Table 5 shows the composition of the feed). The feed product is to be fed to a horse weighing about 500 kg and having dry, flaky skin and dull hair coat. It is to be observed an improvement in the skin conditions after feeding an effective amount of the feed product to the horse. It is to be shown that the effective dose of oil providing beneficial effects on the skin for a 500 kg horse is estimated to contain 40-45 g of oil derived from hempseed and linseed. The oil content of hempseed press cake is to be about 17% and the oil content in linseed press cake is to be about 17%. Some linseed oil is to be added to the feed to increase the ratio of LA and ALA to 2:1.

TABLE 6

Composition of the feed product made in Example 16 comprising a mixture of press cake and full fat oil seed.

| Contents | g/kg |
|---|---|
| Hempseed press cake | 500 |
| Ground full fat hempseed | 160 |
| Linseed press cake | 50 |
| Linseed oil | 5 |
| Source of starch (grain) | 235 |
| Molasses | 50 |
| Mixed tocopherols, μg/g of oil | 2000 |

Source of starch e.g. grain is used in the feed mixture to improve the hardness of the pellet and molasses is used to improve the palatability of the pellet. These feed ingredients can be replaced by others known in the business of making horse feed. Additional pelletizing agents may be needed.

EXAMPLE 17

Previous examples all involve use of a nutritional oil blend with a composition presented in table 7.

TABLE 7

Composition of the nutritional oil blend referred to in examples 1 through 12

| Contents[1] | g/kg |
|---|---|
| Hempseed oil (Finola variety) | 500 |
| Rapeseed oil | 447 |
| Linseed oil | 50 |
| Mixed tocopherols | 3 |

[1]All oils used in the nutritional oil blend are cold pressed and processed into a blend without filtration.

Fatty acid profile of the nutritional oil blend according to example one (Table 7) is presented in Table 8. The fatty acid profile includes additional parameters such as the level of LA+ALA and GLA+SDA (% of total fatty acids) and LA:ALA ratio. These additional parameters are relevant when the nutritional oil blend according to example 1 is formulated by using different varieties of ingredient oils.

TABLE 8

Lipid composition of the nutritional oil blend
Fatty acids (% of total fatty acids)

| | |
|---|---|
| 16:0 | 4.4 |
| 18:0 | 2.0 |
| 18:1 (n-9) | 29.3 |
| 18:2 (n-6); LA | 34.3 |
| 18:3 (n-6); GLA | 2.0 |
| 18:3 (n-3); ALA | 17.8 |
| 18:4 (n-3); SDA | 1.0 |
| LA + ALA | 52.1 |
| GLA + SDA | 3.0 |
| LA:ALA | 1.9 |

Hempseed oil, rapeseed oil and linseed oil contain essential fatty acids, linoleic acid (LA) and alpha-linolenic acid (ALA). In addition, hempseed oil contains appreciable levels immediate metabolites of LA and ALA, gamma-linolenic acid (GLA) and stearidonic acid (SDA). Presence of these fatty acids in the nutritional oil blend at 3% of total fatty acids is likely to contribute in part to the beneficial skin health effects observed. Thus it is important to recognize that in the hempseed oil used as an ingredient in manufacture of the nutritional oil blend according to the example 1, the levels of GLA and SDA may vary. Table 9 presents the fatty acid composition of four different varieties of hempseed oil where the GLA and SDA levels vary from 9% ('Maximum') to 1.3% ('Very low') of total fatty acids, with 'Typical' and 'Low' types of hempseed oil having intermediate levels of GLA and SDA.

TABLE 9

Fatty acid composition of different varieties
of hempseed oil (% of total fatty acids)

| | Maximum[1] | Typical[2] | Low[3] | Very low[4] |
|---|---|---|---|---|
| C16:0 | 6.0 | 6.4 | 6.5 | 7.0 |
| C18:0 | 2.4 | 2.4 | 2.5 | 3.2 |
| C18:1 oleic acid (OA) | 8.6 | 8.3 | 11.0 | 15.2 |
| C18:2 linoleic acid (LA) | 51.9 | 54.8 | 57.0 | 56.2 |
| C18:3 α-linolenic acid (ALA) | 21.2 | 19.2 | 18.0 | 16.0 |
| C18:3 γ-linolenic acid (GLA) | 6.8 | 4.4 | 2.7 | 0.94 |
| C18:4 stearidonic acid (SDA) | 2.5 | 1.7 | 0.6 | 0.39 |
| LA:ALA | 2.4 | 2.9 | 3.2 | 3.5 |
| LA + ALA | 73.1 | 74.0 | 75.0 | 72.2 |
| GLA + SDA | 9.0 | 6.1 | 3.3 | 1.3 |

[1]Maximum observed GLA and SDA concentrations in hempseed oil according to Matthäus and Bruhl (2008); other fatty acids as in FIN-314 (Callaway et al. 2007)
[2]Oil from Finola variety of hempseeds grown in Canada; sample supplied by HempOil Canada and analyzed by the authors
[3]Sample of Chinese hempseed oil (Mölleken & Theimer 2007)
[4]Oil from Kompolti variety of hempseeds grown in Hungary (Callaway et al. 2007)

As shown above, GLA and SDA contents in hempseed oil are likely to be the most variable fatty acid components in the nutritional oil blend. In order to formulate the nutritional oil blend according to example 1 by using different hempseed oil varieties, the level of GLA+SDA in the blend needs to be fixed to a minimum concentration of 3% of total fatty acids. As the LA:ALA ratio is also considered to be an important contributor to the biological effect, the ratio is allowed to vary minimally between 1.9:1 and 1.99:1. Novel oil blends presented in Table 10 were produced by using 'Maximum', 'Typical', 'Low' and 'Very low' types of hempseed oil.

TABLE 10

Proportions of different ingredient oils (%) and fatty acid
profiles (% of total fatty acids) of the nutritional oil
blends made using four different varieties of hempseed oil

| | Blend 'Typical' | Blend 'Maximum' | Blend 'Low' | Blend 'Very low' |
|---|---|---|---|---|
| Oils, % | | | | |
| Hempseed oil | 50.0 | 35.0 | 65.0 | 65.0 |
| Rapeseed oil | 42.7 | 62.7 | 20.0 | 13.7 |
| Linseed oil | 7.0 | 2.0 | 11.0 | 12.0 |
| Borage oil | — | — | — | 3.0 |
| *Echium* oil | — | — | 3.7 | 6.0 |
| Tocopherols | 0.3 | 0.3 | 0.3 | 0.3 |
| Fatty acids, % of total fatty acids | | | | |
| 18:1 (n-9); OA | 30.3 | 39.8 | 20.7 | 30.0 |
| 18:2 (n-6); LA | 36.3 | 30.1 | 41.5 | 40.8 |
| 18:3 (n-3); ALA | 18.6 | 15.5 | 21.6 | 21.3 |
| 18:3 (n-6); GLA | 2.2 | 2.4 | 2.2 | 1.9 |
| 18:4 (n-3); SDA | 0.9 | 0.9 | 0.8 | 1.1 |
| LA + ALA | 54.9 | 45.5 | 63.1 | 62.1 |
| GLA + SDA | 3.1 | 3.3 | 3.0 | 3.0 |
| LA:ALA | 1.95 | 1.95 | 1.94 | 1.92 |

It can be observed that different types of hempseed oil can be used in formulating the nutritional oil blend according to example 1. Target level of GLA+SDA of minimum 3.0% can be obtained by varying the amount of hempseed oil used in the blend or by supplementing the blend with oils rich in GLA and SDA such as borage oil and echium oil. Furthermore, the level of linseed oil can be subsequently adjusted in the blend to produce the target ratio of LA and ALA of 1.9 to 1.99. The levels of LA+ALA and OA in the blend are allowed to vary between 45 to 63% and 21 to 40% of total fatty acids, respectively.

It can be further observed that each of the novel blends is clearly distinguishable from the FIN-314 type hempseed oil, the variety used in the dietary supplementation study involving human subjects with atopic dermatitis [12].

TABLE 11

Comparison of the parameters of fatty acid composition between
the nutritional oil blends and the FIN-314 type hempseed oil.

| | Nutritional oil blend | Hempseed oil |
|---|---|---|
| LA:ALA | 1.92 to 1.95 | 2.8 |
| LA + ALA, % of total fatty acids | 45.5 to 63.1% | 76.0% |
| OA, % of total fatty acids | 20.7 to 39.8% | 8.3% |
| GLA + SDA, % of total fatty acids | 3.0 to 3.3% | 6.0% |

The nutritional oil blend according to the invention can also be formulated without hempseed oil by using a variety of different plant oils and fixing the LA:ALA ratio (1.9 to 1.99) and GLA+SDA content (min. 3.0% of total fatty acids).

TABLE 12

Formulating the nutritional oil blends without hempseed oil.

|  | Blend a | Blend b | Blend c | Blend d |
|---|---|---|---|---|
| Oils, % | | | | |
| Rapeseed oil | — | 15.0 | — | — |
| Soybean oil | 55.0 | — | — | — |
| Safflower oil | — | 41.0 | — | — |
| Sunflower oil | — | 6.0 | 53.0 | 45.0 |
| Evening primrose oil | 11.0 | — | — | — |
| *Echium* oil | 9.0 | 9.0 | — | — |
| Linseed oil | 25.0 | 29.0 | 36.0 | 34.0 |
| Borage oil | — | — | — | — |
| *Echium* oil | — | — | — | — |
| GMO canola oil | — | — | 4.5 | 9.0 |
| GMO soybean oil | — | — | 6.0 | 12.0 |
| Fatty acids, % of total fatty acids | | | | |
| 18:1 (n-9); OA | 20.9 | 21.7 | 21.1 | 20.9 |
| 18:2 (n-6); LA | 41.3 | 41.9 | 42.5 | 40.1 |
| 18:3 (n-3); ALA | 21.4 | 21.5 | 21.6 | 21.1 |
| 18:3 (n-6); GLA | 2.0 | 2.2 | 2.0 | 4.0 |
| 18:4 (n-3); SDA | 1.1 | 1.1 | 1.0 | 2.0 |
| LA + ALA | 62.6 | 63.4 | 64.1 | 61.2 |
| GLA + SDA | 3.1 | 3.2 | 3.0 | 6.0 |
| LA:ALA | 1.93 | 1.95 | 1.97 | 1.90 |

Further examples on the use of the nutritional oil blend based on case histories. Case histories include age, sex and breed of the animal, description of the specific condition and past treatment history including dietary use of other oils that failed to alleviate the condition.

EXAMPLE 18

As shown in example 4, nutritional oil blend improved the dry, rough and chapped paw pads of ten dogs in a follow up study. During the 12 week supplementation period the paw pads became smoother and more supple. It was not evident whether these types of improvements in paw pads would increase the durability of the paw pads in strenuous exercise and work. Therefore, two groups of working dogs were followed up.

Several male and female Greyhounds owned by one trainer had had a condition in the past where a small stone penetrates the skin of the paw pad, becomes lodged in the tissue in a way that requires surgical removal. Five greyhounds were supplemented with the nutritional oil blend prepared as in example 1 at 4 ml/10 kg of body weight and followed up for one year. Dogs were trained and raced as before, but experienced no longer any problems with the small stones penetrating the paw pads. This result indicates that the effect of the nutritional oil blend improving the condition of rough and chapped paw pads also improves the durability of the paw pads in dogs performing strenuous exercise.

Eight male or female Finnish Hounds were recruited in a follow up to examine the effect of the nutritional oil blend prepared as in example 1 on the durability of the paw pads in dogs performing work in harsh conditions of wet, rough and frozen grounds. Conditions, which often produce cracks and wounds in the paw pads. Oil supplementation at 4 ml/10 kg body weight level was started at least two months before the hunting season commenced. The owners of the dogs reported a clear tendency towards reduced incidence of cracks and wounds in the paw pads among the dogs that were supplemented with the nutritional oil blend. Thus, it is concluded that a nutritional oil blend that makes paw pads smooth and supple also increases the durability of the paw pads in hunting dogs performing strenuous exercise.

EXAMPLE 19

A five year old, male French Bulldog had a dry, rough and chapped rhinarium (nose). In this breed of dogs the rhinarium is typically black, but for this individual the black colour of the rhinarium had faded and was grey. Various nutritional supplements like biotin and vitamin A had been used without any appreciable effect on the appearance of the rhinarium. Topical treatment with oil or ointments provided temporary smoothing effect and a change in colour. Supplementation with a nutritional oil blend as prepared in example 1 resulted in a gradual improvement in the condition of the rhinarium. After more than two months of supplementation the condition of the rhinarium was markedly improved. The rhinarium was no longer rough and chapped, but it was supple and had obtained a characteristic black colour. Subsequently the positive effect on the rhinarium condition was produced with the oil blend in dogs from different breeds.

EXAMPLE 20

A three year old, female Bullterrier Dog had suffered from various skin problems since it was a puppy. The skin problems were characterized by red spots in the stomach and hairless spots in the head and in the hind limbs. In addition to the skin problems the dog suffered from splitting and breaking claws. The claws kept constantly breaking and by the age of three the claws had never grown long enough to be clipped. The dog had been treated with biotin for the claws and various nutritional formulations containing gamma-linolenic acid and fish oil fatty acids for the skin without any appreciable improvement in either the claws or skin condition. Supplementation with a nutritional oil blend as prepared in example 1 was started and it resulted in a clear improvement of the skin condition within two months. The skin was cleared from the red spots and the hairless areas started to grow hair. The positive effects on the skin health remained over several months as the supplementation was continued. The dog also developed strong claws during supplementation. Three months after the supplementation with the oil blend had begun, the dog's claws needed to be clipped. This was the first time in this dog's life.

EXAMPLE 21

A four year old, female schapendoes dog was diagnosed with symmetrical lupoid onychodystrophy (SLO). The dog was initially treated for secondary bacterial infections in some of the affected claws with cephalexin resulting in total resolution of the bacterial infection. Supplementation with the nutritional oil blend as prepared in example 1 at 4 ml/10 kg body weight was started immediately after the secondary infections had cleared. The claws grew back during supplementation and the dog remained without symptoms at least five months which was the length of the follow up.

EXAMPLE 22

In some dogs the imbalance of skin lipids may express itself as superficial lesions and crusting of the skin. Associated secondary infections often require medication with antibiotics. An imbalance of the skin lipids and/or lipid metabolism of the skin can be suspected when the condition responds to supplementation with nutritional oil blend prepared as in example 1. Two dogs with recurrent skin problems, five year old male German Shepherd and nine year old female Lapp Reindeer dog were successfully weaned off medications after two months of nutritional oil use. Skin remained healthy as long as the supplementation with the nutritional oil continued.

EXAMPLE 23

Six year old female Whippet had localized hair loss in the head. There was no itching or other problems associated with the hair loss. Condition had persisted over a long period of time. Thus the hair loss was considered a chronic condition. Supplementation with nutritional oil blend prepared as in example 1 resulted in regrowth of hair that had similar colour and appearance as the hair in other parts of the skin.

EXAMPLE 24

Irritation of the dog skin due to various external irritants is sometimes expressed as reddening of the skin in the feet, especially between the toes. The dog licks the feet which often worsens the condition. Two dogs with this condition, a 4 year old female Chromphorländer and a seven year old male Wire-haired Dachshund were supplemented with the nutritional oil blend prepared as in example 1. Condition of the skin between the toes improved in both dogs within two months of supplementation. The Chromphorländer had previously been given linseed oil and the Dachshund had been given a commercial skin health product based on borage oil and fish oil. This example shows that the nutritional oil is more effective in alleviating irritation of the skin between the toes than dietary supplementation with linseed oil and with commercial product based on borage oil and fish oil.

EXAMPLE 25

Seven year old female Jack Russell Terrier with recurrent external ear infections due to yeast (*Malassezia pachydermatis*) was treated repeatedly with Posatex drops. After the nutritional supplementation with the oil blend prepared as in example 1 was started, the dog did not relapse any more. Disease free period continued at least for one year of follow up. Although the nutritional oil is not likely to be anti-fungicidal it appears to improve the efficacy of the anti-fungicidal treatment. It is likely that nutritional supplementation with the oil blend improved the health of the skin inside the ears and thus reduced the susceptibility of the ear to yeast infections.

EXAMPLE 26

Skin condition of twenty dogs of different breeds was followed up for two months in a survey conducted among owners of agility dogs. Dogs with clinical symptoms of nutritional dermatosis i.e. dull hair coat, excessive shedding, dry or greasy skin and desquamation were enrolled. During the two-month period the dogs were supplemented with the nutritional oil prepared as in example 1. In the beginning of the follow up the owners were given a questionnaire with questions about the skin condition of their dog, diet specifics and use of nutritional supplements. After two months of supplementation the owners were asked about any changes in the skin condition. Before the supplementation period the surveyed dogs had been given food oils like rapeseed oil and olive oil or specialty oils marketed for dogs including salmon oil and linseed oil or commercial products based on fish oil and borage oil blends (source of GLA). In summary, 17/20 owners of dogs with clinical symptoms of nutritional dermatosis reported significant improvement in hair coat (e.g. increased shine), reduced shedding of hair, reduced dryness of the skin and reduced desquamation. Remaining 3/20 owners reported some improvement. This survey demonstrated that the nutritional oil blend prepared as in example 1 is effective in alleviating clinical signs of nutritional dermatosis and it appears to be more effective than the nutritional oils commonly used for dogs.

EXAMPLE 27

After successful alleviation of skin problems with the nutritional oil blend prepared as in example 1 the supplementation was discontinued in several dogs. When nutritional supplementation with the oil was discontinued, relapse of clinical symptoms occurred in these dogs. After resumption of supplementation the skin condition was improved again. Cases of skin problems followed up through discontinuation/relapse and resumption of supplementation/improvement of the skin condition phases include localized hair loss in a 6 year old female whippet, superficial ulceration/crusting in a five year old male German Shepherd, hot spots in a 2 year old male Saleros El Bueno and furunculosis in a 12 year old male Labrador Retriever. These examples demonstrate that in some cases the underlying problem in lipid metabolism alleviated by the nutritional oil blend may persist and lifelong supplementation with nutritional supplements may be required.

EXAMPLE 28

A survey was performed among pet dog owners, owners of show dogs and hunting dogs as well as professional dog groomers who had tested the nutritional oil prepared as in example 1 for at least two months. Results of this survey indicate that supplementation of dogs with the nutritional oil blend results in improved maintenance of skin and hair coat in healthy animals. Following observations were provided by the survey:

Daily maintenance of a pet dogs becomes easier. Hair coat does not get dirty as easily and less frequent washing is needed. Also, long and silky hair becomes less tangled and thus brushing is easier.

In show dogs, the hair coat becomes, what is considered to be characteristic for a specific breed in terms of silkiness, coarseness, shine, colour etc. and the maintenance of the hair coat by brushing, plucking and other means of grooming also becomes easier.

Regular use of the nutritional oil blend normalizes the moulting cycle of the dog. Apparently the maturation of growing hair becomes better synchronized and the dog assumes the natural semi-annual moulting cycle instead of shedding hair continuously.

Hair coat of hunting dogs (e.g. Finnish Hound and East Siberian Laika) working in wet conditions do not get thoroughly wet and thus demonstrate a decrease in lowest comfort temperature.

EXAMPLE 29

A feed product for horses as described in examples 15 and 16 was prepared by replacing linseed containing hempseed presscake with, camelina presscake. Camelina is an oilseed rich in alpha-linolenic acid, but it does not contain mucins as linseed does. Thus camelina containing feeds don't have to be soaked in water prior to feeding to the animals. Camelina press cake is also more palatable to the horse than linseed press cake. Fatty acid profile and mixed tocopherol content are essentially the same as the feed product prepared according to example 15. The feed product containing camelina press cake instead of linseed press cake reduced incidence/severity of summer eczema in horses.

TABLE 13

Composition of the feed product made in Example 29, comprising hempseed and camelina press cakes.

| Contents | g/kg |
|---|---|
| Hempseed press cake | 700 |
| Camelina press cake | 175 |
| Source of starch (grain) | 100 |
| Molasses | 25 |
| Mixed tocopherols, µg/g of oil | 2000 |

EXAMPLE 30

Cats are carnivores and they lack delta-6 desaturase enzyme responsible for metabolizing essential fatty acids. Therefore it is not likely that a nutritional oil blend, as prepared in example 1, a product characterized with a high level of essential fatty acids, linoleic acid and alpha-linolenic acid, would demonstrate a beneficial effect in cats. Therefore, it was unexpected that nutritional oil blend as prepared in example 1 and fed at 4 ml/10 kg to British Shorthair cats with dull hair coat and desquamation resulted in improvement of the hair and skin condition.

EXAMPLE 31

Nutrolin oil was fed to rats, mice, hamsters, guinea pigs and gerbils at 1 ml/kg of body weight. Also, the pelleted feed product formulated for horses according to example 15 was fed to rabbits providing approximately 1 ml/kg oil. The supplements were well tolerated and apparent improvement of the hair coat (shine and colour) was observed.

REFERENCES

1. Harvey, R. G. 1993. Nutritional therapy. In: BSAVA Manual of Small Animal Dermatology. Ed. Harvey, R. G. & Mason, I. S. British Small Animal Veterinary Association s. 244-250.
2. Watson, T. D. G. 1998. Diet and skin disease in dogs and cats. Journal of Nutrition 128: S2783-S2789.
3. Kirby N. A., Hester, S. L. and Bauer, J. E. 2007. Dietary fats and the skin and coat of dogs. JAVMA 230:1641-1644.
4. Campbell, K. D. and Dorn, G. P. 1992. Effects of oral sunflower oil and olive oil on serum and cutaneous fatty acids concentrations in dogs. Research in Veterinary Science 53: 172-178.
5. Logas, D. and Kunkle, G. 1994. Double-blinded crossover study with marine oil supplementation containing high-dose eicosapentaenoic acid for the treatment of canine pruritic skin disease. Veterinary Dermatology 5: 99-104.
6. Rees, C. A., Bauer, J. E. and Burkholder, W. J. 2001. Effects of dietary flax seed and sunflower seed supplementation on normal canine serum polyunsaturated fatty acids and skin and hair coat conditions scores. Vet. Dermatol. 12:111-117.
7. Sture, C. H., and Lloyd, D. H. 1995. Canine atopic disease: therapeutic use of an evening primrose oil and fish combination. Vet. Rec. 137:169-170.
8. Noli C, Carta G, Cordeddu L, Melis M P, Murru E, Banni S. 2007. Conjugated linoleic acid and black currant seed oil in the treatments of canine atopic dermatitis: a preliminary report. Vet J. 173(2):413-21.
9. Saevik, B. K., Bergvall, K., Holm, B. R., Saijonmaa-Koulumies, L. E., Hedhammar, A., Larsen, S. and Kristensen, F. 2004. A randomized, controlled study to evaluate the steroid sparing effect of essential fatty acid supplementation in the treatment of canine atopic dermatitis. Vet. Dermatol. 15:137-145.
10. Anonymous, 2006. Nutritional requirements of dogs and cats. National Research Council. The National Academies Press, Washington. pp 398.
11. Miller C. C. and Ziboh V. A. 1988. Gamma-linolenic acid enriched diet alters cutaneous eicosanoids Biochem Biophys Res Commun 154(3):967-74.
12. Callaway, J., Schwab, U., Harvima, I., Halonen, P., Mykkanen, O., Hyvonen, P. and Jarvinen, T. J. 2005. Dermatological Treatment, 16, 87-94.
13. Björnsdóttir, S., Sigvaldadóttir, J., Broström, H., Langvad, B., and Sigurðsson, A. 2006. Summer eczema in exported Icelandic horses: influence of environmental and genetic fators. Acta Vet. Scand. 48:1-4.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in medicine, biochemistry, or related fields are intended to be within the scope of the following claims.

The invention claimed is:

1. A lipid composition comprising linoleic acid (LA), alpha-linolenic acid (ALA), stearidonic acid (SDA) and gamma linolenic acid (GLA), said LA and ALA in a ratio of from about 1.5:1 to about 2.39:1, said GLA to said SDA in a ratio of at least 2:1, said LA to said GLA in a ratio of at least 10:1, said ALA to said SDA in a ratio of at least 10:1 and said lipid composition comprising greater than about 3% SDA and GLA as determined by gas chromatography, wherein said lipid composition comprises a mixture of natural tocopherols ($\alpha$, $\beta$, $\gamma$, $\delta$) and is essentially free of EPA and DHA.

2. The composition of claim 1, wherein the said ratio of LA to said ALA is at least 2:1 as determined by gas chromatography.

3. The composition of claim 1, wherein the ratio of said LA to said GLA is at least 20:1 and the ratio of said ALA to said SDA is at least 20:1 as determined by gas chromatography.

4. The composition of claim 1, wherein said LA, said ALA, said GLA and said SDA are obtained from linseed oil, rapeseed oil and/or hempseed oil.

5. The composition of claim 1, wherein said LA, said ALA, said GLA and/or said SDA are obtained from the group consisting of oil seed press cakes selected from the group consisting of linseed, hempseed and camelina seed as well as linseed oil, full fat linseeds, hempseed oil and full fat hempseed.

6. A lipid mixture comprising the lipid composition of claim 1 effective on alleviating skin problems in companion animals.

7. A method comprising administering the composition of claim 1 to a companion animal in an amount effective for improving or treating a condition selected from the group consisting of: eczema, dry skin, flaky skin, pruritus, pyotraumatic dermatitis, furunculosis, dry paw pads, rough paw pads, chapped paw pads, paw pad durability, dry rhinarium, chapped rhinarium, split claws, brittle claws, rashes, hairless spots, hot spots, symmetrical lupoid onychodystrophy, skin ulceration, skin crusting, reddening of skin between toes, external ear infection, and nutritional dermatosis.

8. The method in claim 7, wherein said companion animal is selected from the group consisting of a dog, cat, horse, rabbit, rat, mouse, hamster, guinea pig and gerbil.

9. A method comprising administering the composition of claim 1 to a companion animal in an amount effective for improving the skin, hair, rhinarium or paw pads of said animal.

10. A method comprising administering the composition of claim 1 to a companion animal in an amount effective to improve atopic and pruritic skin conditions, wherein said companion animal is selected from the group consisting of a dog, cat, horse, rabbit, rat, mouse, hamster, guinea pig and gerbil.

* * * * *

UNITED STATES PATENT AND TRADEMARK OFFICE
CERTIFICATE OF CORRECTION

PATENT NO. : 8,470,876 B2
APPLICATION NO. : 13/132382
DATED : June 25, 2013
INVENTOR(S) : Bruheim et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 106 days.

Signed and Sealed this
Eighth Day of September, 2015

Michelle K. Lee
*Director of the United States Patent and Trademark Office*